United States Patent [19]

Saito et al.

[11] Patent Number: 4,500,346

[45] Date of Patent: Feb. 19, 1985

[54] SUBSTITUTED PHENOXYPROPIONATES AND HERBICIDAL COMPOSITIONS CONTAINING SAME AND THEIR HERBICIDAL USE

[75] Inventors: Junichi Saito; Kazuomi Yasui, both of Tokyo; Kozo Shiokawa, Kanagawa; Atsumi Kamochi, Tokyo, all of Japan

[73] Assignee: Nihon Tokushu Noyaku Seizo K.K., Tokyo, Japan

[21] Appl. No.: 483,974

[22] Filed: Apr. 11, 1983

[30] Foreign Application Priority Data

Apr. 20, 1982 [JP] Japan .................................. 57-64702

[51] Int. Cl.³ ..................... C07D 213/64; A01N 43/40
[52] U.S. Cl. .......................................... 71/94; 546/300; 546/301; 546/302; 560/226; 560/229; 560/62
[58] Field of Search ....................... 546/302, 300, 301; 71/94

[56] References Cited

FOREIGN PATENT DOCUMENTS 0030702 6/1981 European Pat. Off. ............ 564/256

Primary Examiner—Alan L. Rotman
Attorney, Agent, or Firm—Sprung, Horn, Kramer & Woods

[57] ABSTRACT

Novel substituted phenoxypropionates of the formula

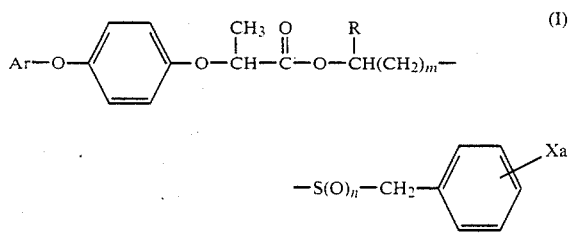

in which
Ar represents the group

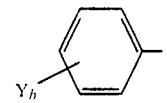

or the group

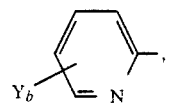

in which
Y represents a halogen atom or a trifluoromethyl group and
b is 1 or 2,
R represents a hydrogen atom or a methyl group,
X represents a hydrogen atom, a halogen atom, a nitro group, a lower alkyl group or a lower alkoxy group,
a and m each independently is 1 or 2, and
n is 0, 1 or 2,
and their use as herbicides.

Novel intermediates of the formulae

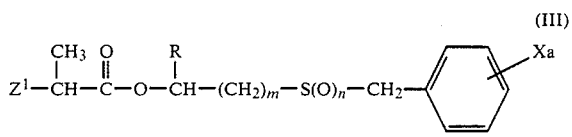

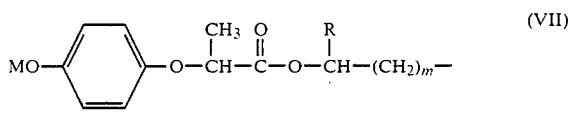

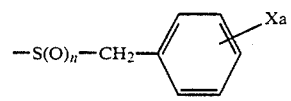

in which formulae
R, X, m, n and a have the meanings given above,
$Z^1$ is a halogen atom and
m is a hydrogen atom or an alkali metal atom.

14 Claims, No Drawings

SUBSTITUTED PHENOXYPROPIONATES AND HERBICIDAL COMPOSITIONS CONTAINING SAME AND THEIR HERBICIDAL USE

The present invention relates to certain novel substituted phenoxypropionates, to herbicidal compositions containing them and to methods of combating weeds utilizing such compounds.

The invention also relates to novel intermediates for the preparation of said substituted phenoxypropionates.

It has already been disclosed in the German Published Specification No. 2,617,804 (corresponding to Japanese Laid-open Patent Application No. 131,545-1977) that herbicidal activity is possessed by compounds of the general formula

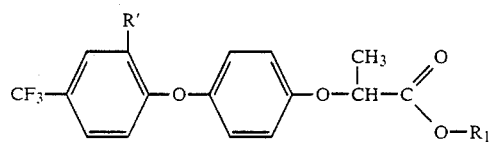

wherein
R' represents hydrogen or halogen,
$R_1$ represents:
(a) straight- or branched chain $(C_1-C_{12})$ alkyl (which is mono- or polysubstituted by cyclohexyl, halophenyl, nitrophenyl, $(C_1-C_6)$ alkylphenyl, phenoxy (which is mono- to trisubstituted in some cases with halogen and/or $(C_1-C_4)$ alkyl), $(C_5-C_6)$ alkoxy, $(C_5-C_6)$alkoxy-$(C_2-C_4)$ alkoxy, $(C_1-C_4)$ alkoxyethoxyethoxy, $(C_1-C_4)$ acyl, a group represented by the general formula

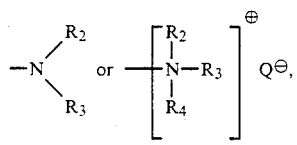

or, in the 2 position or a position remote from the carboxyl, mono- or poly-substituted by phenyl);
(b) cyclohexenyl or phenyl-$(C_3-C_4)$alkenyl;
(c) $(C_3-C_4)$alkynyl (which is optionally mono- or di-substituted by straight or branched chain $(C_1-C_4)$ alkyl, halogen, phenyl, halophenyl or $(C_1-C_4)$ alkylphenyl), provided that $R_1$ does not represent unsubstituted propargyl or butynyl;
(d) one of the groups represented by the following general formulae:

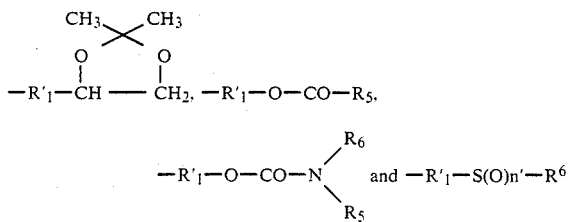

or
(e) $(C_1-C_2)$alkyl substituted by furyl, tetrahydrofuryl, pyridyl or oxiranyl,
$R_2$ represents hydrogen, $(C_1-C_4)$alkyl or $(C_1-C_4)$-alkoxy,
$R_3$ represents hydrogen, $(C_1-C_4)$alkyl or phenyl, or
$R_2$ and $R_3$ together form a 4- or 5-membered, saturated or unsaturated alkylene chain one methylene of which may optionally be replaced by

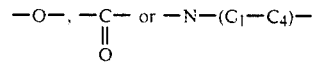

alkyl,
$R_4$ represents hydrogen or $(C_1-C_4)$alkyl,
Q represents an inorganic or organic anion,
$R_1'$ represents straight or branched chain $(C_1-C_{12})$alkylene,
$R_5$ represents hydrogen, $(C_1-C_4)$alkyl, $(C_1-C_4)$-haloalkyl, phenyl optionally substituted by halogen, nitro and/or $(C_1-C_4)$ alkyl, or a group represented by the formulae

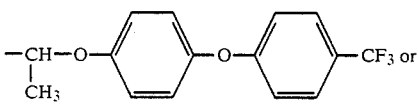

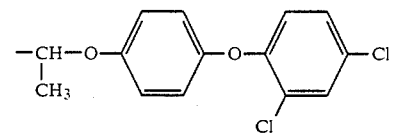

$R_6$ represents $(C_1-C_4)$alkyl, and
n' is 0, 1 or 2.

The German Published Specification No. 2,812,571 (corresponding to Japanese Laid-open Patent Application No. 119,476-1979) teaches herbicidally active compounds of the general formula

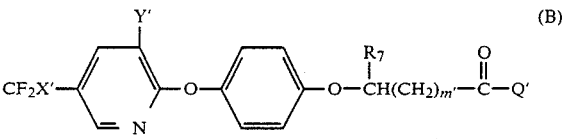

in which
X' represents fluorine or chlorine,
Y' represents hydrogen or chlorine,
$R_7$ represents hydrogen, methyl or ethyl,
m' is 0 or 2, and
Q' represents hydroxy, $(C_1-C_6)$alkoxy whose alkyl moiety is optionally substituted by 1 to 3 halogen, $(C_1-C_4)$alkoxy-$(C_1-C_4)$alkoxy, $(C_2-C_4)$alkenyloxy, $(C_2-C_4)$alkynyloxy, $(C_3-C_6)$cycloalkyl whose cycloalkyl moiety is optionally substituted by $(C_1-C_4)$alkyl, $(C_1-C_4)$alkoxycarbonyl-$(C_1-C_4)$alkoxy, phenoxy whose phenyl moiety is optionally substituted by 1 to 3 halogen or $(C_1-C_4)$alkyl, benzyloxy, glycidyloxy, $(C_1-C_4)$alkylthio, $(C_2-C_4)$alkenylthio, phenylthio whose phenyl moiety is optionally substituted by 1 to 3 halogen or $(C_1-C_4)$alkyl, amino, $(C_1-C_4)$-alkylamino, $(C_1-C_4)$alkoxycarbonylmethylamino, hydroxycarbonylmethylamino, anilino group whose phenyl moiety may optionally be substituted by 1 to 3 halogen, pyridin-2-ylamino, an —O— cation, or halogen.

The herbicidal activity of the afore-mentioned compounds, however, is not always completely satisfactory.

The present invention now provides, as new compounds, the substituted phenoxypropionates of the general formula

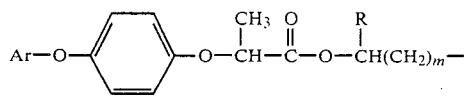
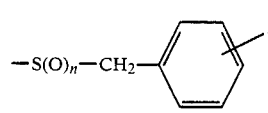
(I)

in which
Ar represents the group

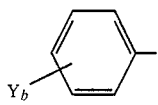

or the group

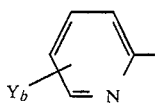

in which Y represents a halogen atom or a trifluoromethyl group and b is 1 or 2, R represents a hydrogen atom or a methyl group, X represents a hydrogen atom, a halogen atom, a nitro group, a lower alkyl group or a lower alkoxy group, a and m each independently is 1 or 2, and
n is 0, 1 or 2.

The substituted phenoxypropionates of the general formula (I) can be prepared by a process,
in which
(a) a compound of the general formula

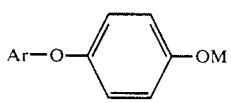
(II)

in which
Ar has the meaning given above and
M represents a hydrogen atom or an alkali metal atom, is reacted with a compound of the general formula

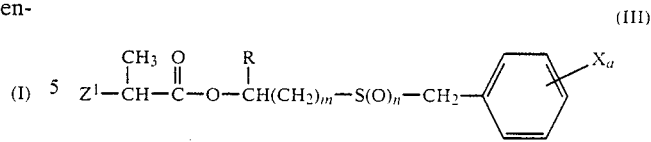
(III)

in which
R, X, a, m and n have the meanings given above, and
$Z^1$ represents a halogen atom,
or
(b) a compound of the general formula

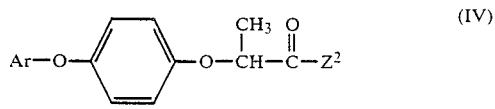
(IV)

in which
Ar has the meaning given above, and
$Z^2$ represents a hydroxyl group or a halogen atom
is reacted with a compound of the general formula

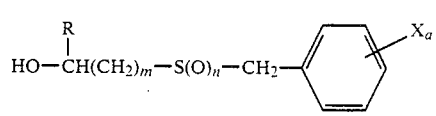
(V)

in which
R, X, a, m and n have the meanings given above, or
(c) a compound of the general formula Ar—$Z^1$ (VI)

in which
Ar and $Z^1$ have the meanings given above, is reacted with a compound of the general formula

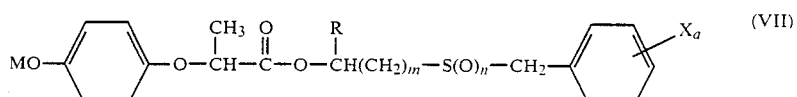
(VII)

in which
R, X, M, a, m and n have the meanings given above,
or
(d) a substituted phenoxypropionate of the general formula

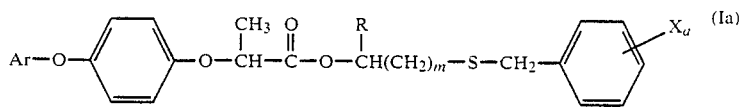
(Ia)

in which
Ar, R, X, a and m have the meanings given above, is reacted with hydrogen peroxide.

The present invention also provides herbicidal compositions comprising as active ingredients substituted phenoxypropionates of the general formula (I). In an additional aspect the present invention provides a method of combating weeds by applying substituted phenoxypropionates of the general formula (I) to the weeds or to their habitat.

Surprisingly the substituted phenoxypropionate compounds of the present invention, which have not previously been described in the literature, can be synthesized with ease in high yield, and are novel active compounds showing excellent selective herbicidal activity against weeds, particularly against gramineous weeds without causing substantial phytotoxicity on agricultural crops. It is particularly surprising that the compounds of the present invention show excellent properties which are not shown by structurally similar prior art compounds, in particular that, coupled with good toleration by useful plants, they show sufficient herbicidal activity in low amounts, and that they control regeneration of weeds, especially perennial gramineous weeds, over a long period of time due to their excellent lasting effect.

The compounds according to the present invention are structurally characterized by the fact that in alkyl esters of substituted phenoxypropionic acids, the alkyl group is substituted by a substituted benzylthio group, a substituted benzylsulfinyl group or a substituted benzylsulfonyl group.

Preferred compounds according to the present invention, and corresponding starting materials are those, in which Ar represents the group or the group

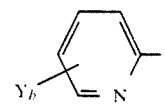

in which

Y represents fluorine, chlorine, bromine, iodine or a trifluoromethyl group, and b is 1 or 2, R represents a hydrogen atom or a methyl group, X represents a hydrogen atom, fluorine, chlorine, bromine, iodine, a nitro group, a methyl, ethyl, propyl, isopropyl, n-butyl, iso-butyl, sec.-butyl or tert.-butyl group, or a methoxy, ethoxy, n-propoxy, iso-propoxy, n-butoxy, iso-butoxy, sec.-butoxy or tert.-butoxy group, a and m each independently is 1 or 2, and n is 0, 1 or 2.

If 4-(4-trifluoromethylphenoxy)-phenol and 2-benzylthioethyl 2-bromopropionate are used as starting materials, the course of reaction variant (a) according to the present invention is illustrated by the following equation:

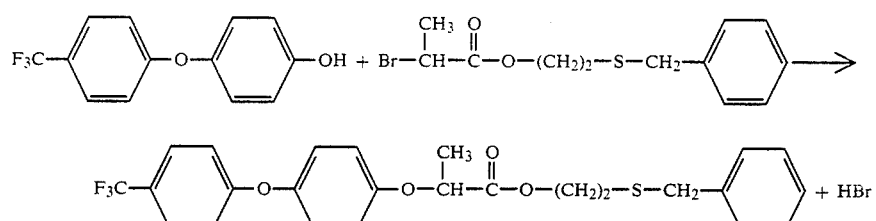

If 2-[4-(4-trifluoromethyl-phenoxy)-phenoxy]-propionyl chloride and 1-benzylthio-2-propanol are used as starting materials, the course of reaction variant (b) according to the present invention is illustrated by the following equation:

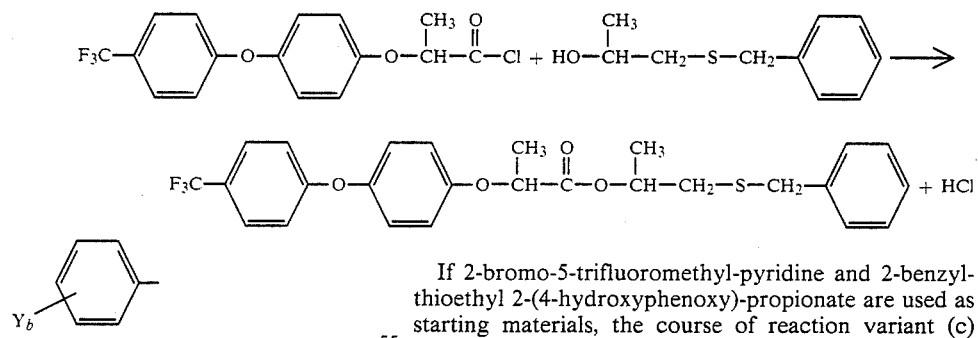

If 2-bromo-5-trifluoromethyl-pyridine and 2-benzylthioethyl 2-(4-hydroxyphenoxy)-propionate are used as starting materials, the course of reaction variant (c) according to the present invention is illustrated by the following equation:

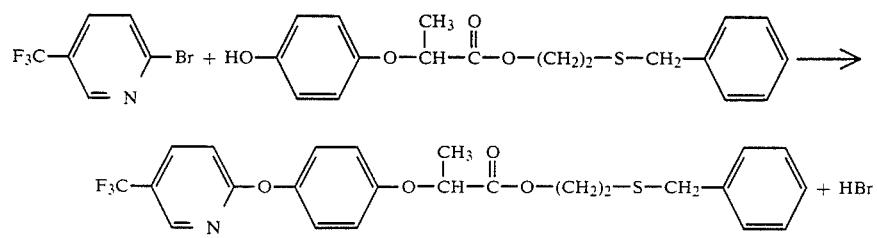

If 2-benzylthioethyl 2-[4-(4-trifluoromethylphenoxy)-phenoxy]-propionate is used as starting material and aqueous hydrogen peroxide is used as oxidizing agent, the course of reaction variant (d) according to the present invention is illustrated by the following equation:

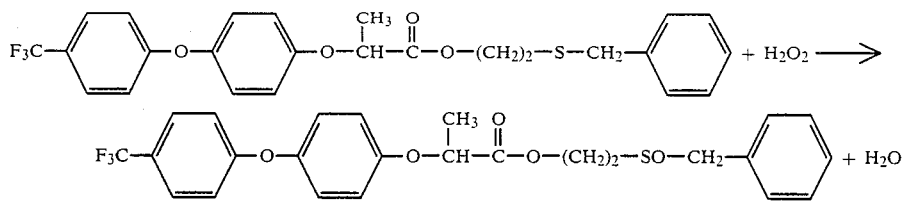

Formula (II) gives an unambiguous definition of the compounds required as starting materials in process (a) according to the invention. In this formula Ar preferably represents those radicals which have already been mentioned in connection with the description of the substituted phenoxypropionates of the formula (I) as being preferred for this radical. The radical M preferably represents hydrogen, lithium, sodium or potassium.

Examples of the compounds of the formula (II) are:
4-(4-trifluoromethyl-phenoxy)-phenol,
4-(4-chloro-2-trifluoromethyl-phenoxy)-phenol,
4-(5-trifluoromethyl-2-pyridyloxy)-phenol, and
4-(3,5-dichloro-2-pyridyloxy)-phenol, as well as their alkali metal salts, such as their sodium, lithium and potassium salts.

Formula (III) gives an unambiguous definition of the compounds required as further starting materials in process (a) according to the invention. In this formula R, X, a, m and n preferably represent those radicals and indices respectively, which have already been mentioned in connection with the description of the substituted phenoxypropionates of the formula (I) as being preferred for said radicals and indices. The radical $Z^1$ preferably represents a chlorine or bromine atom.

Examples of the compounds of the formula (III) are:
2-benzylthioethyl 2-chloro(or bromo)propionate,
1-methyl-2-benzylthioethyl 2-chloro(or bromo)propionate,
3-benzylthiopropyl 2-chloro(or bromo)propionate,
2-(2-fluorobenzylthio)ethyl 2-chloro(or bromo)propionate,
2-(2-chlorobenzylthio)ethyl 2-chloro(or bromo)propionate,
2-(4-chlorobenzylthio)ethyl 2-chloro(or bromo)propionate,
2-(4-methoxybenzylthio)ethyl 2-chloro(or bromo)propionate,
2-(3-nitrobenzylthio)ethyl 2-chloro(or bromo)propionate,
2-(2,4-dichlorobenzylthio)ethyl 2-chloro(or bromo)propionate,
2-benzylsulfinylethyl 2-chloro(or bromo)propionate,
2-(4-methylbenzylthio)ethyl 2-chloro(or bromo)propionate, and
2-benzylsulfonylethyl 2-chloro(bromo)propionate.

Reaction variant (a) according to the present invention is preferably carried out in the presence of a solvent or diluent. For this purpose, any inert solvents and diluents may be employed.

Examples of such solvents and diluents include water; aliphatic, alicyclic and aromatic hydrocarbons—each of which may optionally be chlorinated (such as hexane, cyclohexane, petroleum ether, ligroin, benzene, toluene, xylene, methylene chloride, chloroform, carbon tetrachloride, ethylene chloride, tri-chloroethylene and chlorobenzene), ethers (such as diethyl ether, methyl ethyl ether, diisopropyl ether, dibutyl ether, propylene oxide, dioxane, and tetrahydrofuran), ketones (such as acetone, methyl ethyl ketone, methyl isopropyl ketone, and methyl isobutyl ketone), nitriles (such as acetonitrile, propionitrile, and acrylonitrile), alcohols (such as methanol, ethanol, isopropanol, butanol, and ethylene glycol), esters (such as ethyl acetate and amyl acetate), acid amides (such as dimethylformamide and dimethylacetamide), sulfones and sulfoxides (such as dimethylsulfoxide and sulfolane) and bases (such as pyridine).

The reaction variant (a) is preferably carried out in the presence of an acid-binding agent. As examples of such acid-binding agents, there may be mentioned hydroxides, carbonates, bicarbonates and alcoholates of alkali metals, and tertiary amines such as triethylamine, diethylaniline, pyridine.

Reaction variant (a) can be carried out over a wide range of temperatures. Generally, it is carried out at a temperature between $-20°$ C. and the boiling point of the reaction mixture, preferably between $0°$ C. and $100°$ C.

This reaction variant is preferably carried out under ambient pressure, although it can be effected under elevated or reduced pressure.

Formula (IV) gives an unambiguous definition of the compounds required as starting materials in process (b) according to the invention. In this formula Ar preferably represents those radicals which have already been mentioned in connection with the description of the substituted phenoxypropionates of the formula (I) as being preferred for this radical. The radical $Z^2$ preferably represents a hydroxyl group, a chlorine or bromine atom.

Examples of the compounds of the formula (IV) are:
2-[4-(4-trifluoromethyl-phenoxy)-phenoxy]propionyl chloride,
2-[4-(4-chloro-2-trifluoromethylphenoxy)-phenoxy]-propionyl chloride,
2-[4-(5-trifluoromethyl-2-pyridyloxy)-phenoxy]-propionyl chloride, and
2-[4-(3,5-dichloro-2-pyridyloxy)-phenoxy]-propionyl chloride,
as well as the corresponding bromides and free propionic acids.

Formula (V) gives an unambiguous definition of the compounds required as further starting materials in process (b) according to the invention. In this formula R, X, a, m and n preferably represent those radicals and indices respectively, which have already been mentioned in connection with the description of the substituted phenoxypropionates of the formula (I) as being preferred for said radicals and indices.

Examples of the compounds of the formula (V) are:
2-benzylthioethanol, 1-benzylthio-2-propanol,
3-benzylthio-1-propanol,
2-(2-fluorobenzylthio)ethanol,
2-(2-chlorobenzylthio)ethanol,
2-(4-chlorobenzylthio)ethanol,
2-(4-methoxybenzylthio)ethanol,
2-(3-nitrobenzylthio)ethanol,
2-(2,4-dichlorobenzylthio)ethanol,
2-benzylsulfinylethanol,
2-(4-methylbenzylthio)ethanol, and
2-benzylsulfonylethanol.

Reaction variant (b) according to the present invention is preferably carried out in the presence of a solvent or diluent. With the exception of alcohols, any of the inert solvents or diluents as described hereinbefore for reaction variant (a) is preferably used for reaction variant (b) to obtain the end product with high purity in high yield.

Likewise reaction variant (b) is preferably carried out in the presence of an acid-binding agent as described hereinbefore for reaction variant (a).

Reaction variant (b) can be carried out within the same reaction conditions of temperature and pressure as those mentioned hereinbefore for reaction variant (a).

Formula (VI) gives an unambiguous definition of the compounds required as starting materials in process (c) according to the invention. In this formula Ar preferably represents those radicals which have already been mentioned in connection with the description of the substituted phenoxypropionates of the formula (I) as being preferred for this radical. The radical $Z^1$ preferably represents a chlorine or bromine atom.

Examples of the compounds of the formula (VI) are:
4-chloro(or bromo)-trifluoromethylbenzene,
1,4-dichloro-2-trifluoromethylbenzene,
1-bromo-4-chloro-2-trifluoromethylbenzene,
2-chloro(or fluoro, or bromo)-5-trifluoromethylpyridine,
2,3,5-trichloropyridine, and
2-bromo-3,5-dichloropyridine.

Formula (VII) gives an unambiguous definition of the compounds required as further starting materials in process (c) according to the invention. In this formula R, X, a, m and n preferably represent those radicals and indices respectively, which have already been mentioned in connection with the description of the substituted phenoxypropionates of the formula (I) as being preferred for said radicals and indices. The radical M preferably represents hydrogen, lithium, sodium or potassium.

Examples of the compounds of the formula (VII) are:
2-benzylthioethyl 2-(4-hydroxyphenoxy)-propionate,
1-methyl-2-benzylthioethyl 2-(4-hydroxyphenoxy)-propionate,
3-benzylthioethyl 2-(4-hydroxyphenoxy)-propionate,
2-(2-fluorobenzylthio)-ethyl 2-(4-hydroxyphenoxy)-propionate,
2-(2-chlorobenzylthio)-ethyl 2-(4-hydroxyphenoxy)-propionate,
2-(4-chlorobenzylthio)ethyl 2-(4-hydroxyphenoxy)-propionate,
2-(4-methoxybenzylthio)ethyl 2-(4-hydroxyphenoxy)-propionate,
2-(3-nitrobenzylthio)ethyl 2-(4-hydroxyphenoxy)-propionate,
2-(2,4-dichlorobenzylthio)ethyl 2-(4-hydroxyphenoxy)-propionate,
2-benzylsulfinylethyl 2-(4-hydroxyphenoxy)propionate,
2-(4-methylbenzylthio)ethyl 2-(4-hydroxyphenoxy)-propionate, and
2-benzylsulfonylethyl 2-(4-hydroxyphenoxy)propionate,
as well as their alkali metal salts, such as their lithium, sodium and potassium salts.

In carrying out reaction variant (c) any of the inert solvents or diluents as described hereinbefore for reaction variant (a) is preferably used to obtain the end product with high purity in high yield. Likewise reaction variant (c) is preferably carried out in the presence of an acid-binding agent as described hereinbefore for reaction variant (a).

Reaction variant (c) can be carried out within the same reaction conditions of temperature and pressure as those mentioned hereinbefore for reaction variant (a).

In carrying out process (d) according to the invention, a substituted phenoxypropionate of the general formula (Ia) is reacted with hydrogen peroxide. The starting materials of the formula (Ia) can be synthesized by means of process variants (a), (b) and (c). An example of a compound of the formula (Ia) is 2-benzylthio-ethyl 2-[4-(4-trifluoromethyl-phenoxy)-phenoxy]-propionate.

Depending on the molar ratio of hydrogen peroxide and substituted phenoxypropionate of the formula (Ia) in reaction variant (d), said substituted phenoxypropionates can be converted into those compounds of the formula (I), wherein n is 1 or 2.

Reaction variant (d) according to the present invention is preferably carried out in the prescence of an organic acid, such as acetic acid, and in the presence of an inert solvent or diluent. Examples of such diluents include chlorinated aliphatic hydrocarbons, such as methylene chloride, chloroform, carbon tetrachloride and ethylene chloride.

Reaction variant (d) can be carried out over a certain range of temperatures. Generally, it is carried out at a temperature between $-20°$ C. and $+100°$ C., preferably between $0°$ C. and $80°$ C.

This reaction variant (d) is preferably carried out under ambient pressure, although it can be effected under elevated or reduced pressure.

The intermediate compound of the formula (III), (which may also be used as an intermediate in the production of intermediates of the formula (VII)) have not hitherto been disclosed in the literature and form a further subject of the present invention.

The compounds of the general formula (III) can be prepared by a process, which comprises reacting a compound of the general formula

in which $Z^1$ and $Z^2$ have the meanings given above, with a compound of the general formula

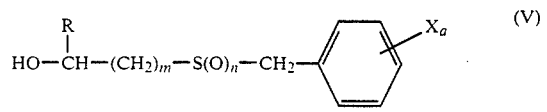

in which

R, X, a, m and n have the meanings given above.

Examples of the compounds of the formula (VIII) used as starting materials in the production of compounds of the formula (III) are: 2-chloropropionic acid and 2-bromopropionic acid as well as the corresponding acid halides, such as chlorides or bromides.

The other starting materials of the formula (V) have already been described above.

If 2-bromopropionyl bromide and 2-benzylthioethanol are used as starting materials, the course of reaction for the production of compounds of the formula (III) is illustrated by the following equation:

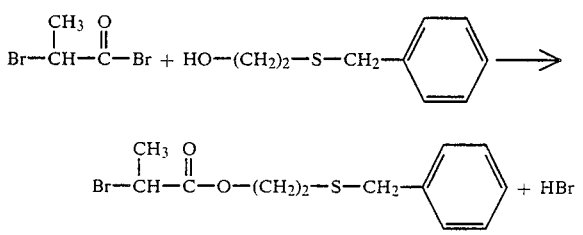

In the process for the production of compounds of formula (III) any of the inert solvents or diluents as described hereinbefore for reaction variant (a), with the exception of alcohols, is preferably used to obtain the end products with high purity in high yield. Likewise this reaction is preferably carried out in the presence of the acid-binding agent as described hereinbefore for reaction variant (a).

The reaction conditions of temperature and pressure are also chosen from those mentioned hereinbefore for reaction variant (a).

The starting compounds of formula (VII) are also novel and form a further subject of the present invention.

The compounds of the general formula (VII) can be prepared by a process, which comprises reacting hydroquinone of the formula

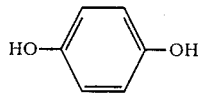

with a compound of the general formula

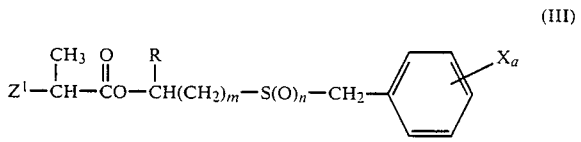

in which R, X, $Z^1$, m, n and a have the meanings given above, and, if appropriate, treating the resulting compounds of the formula (VII), wherein M denotes hydrogen, with an alkali metal hydroxide, carbonate or alcoholate.

Examples of the compounds of the formula (III) used as starting materials have already been mentioned as preferred starting materials for reaction variant (a) and can be prepared as described above.

If hydroquinone and 2-benzylthioethyl-2-bromopropionate are used as starting materials, the course of the reaction for the production of compounds of formula (VII) is illustrated by the following equation:

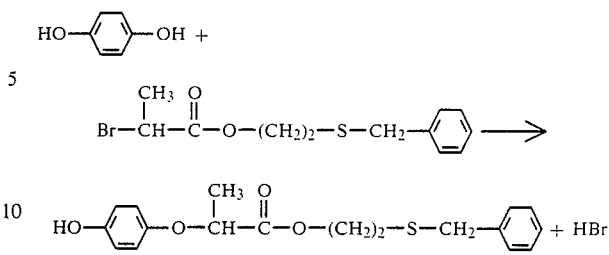

In the process for the production of compounds of formula (VII) any of the inert solvents or diluents as described hereinbefore for reaction variant (a) is preferably used to obtain the end products with high purity in high yield. Likewise this reaction is preferably carried out in the presence of the acid-binding agent as described hereinbefore for reaction variant (a).

The reaction conditions of temperature and pressure are also chosen from those mentioned hereinbefore for reaction variant (a).

The active compounds of formula (I) according to the present invention show excellent selective herbicidal activity. They can be applied either before or after emergence of the plants. They are preferably applied before emergence of the plants, that is to say by the pre-emergence method. They can also be incorporated into the soil before sowing.

Since the active compounds according to the present invention show little or no toxicity towards warm-blooded animals and show good selectivity for agricultural plants, that is cause no phytotoxicity for agricultural plants, they can be conveniently used as herbicides for controlling weeds, particularly for the control of gramineous weeds. By "weeds" in the broadest sense there are meant plants growing in places where they are not desired.

The active compounds according to the present invention may be used, for example, to combat the following plants: *Echinochloa crus-galli* P. Beauv., *Digitaria adscendens* Henr., *Eleusine indica* Gaertn., *Setaria Viridis* P. Beauv., *Avena fatua*, *Alopecurus aequalis* var. amurensis Ohwi, *Setaria lutescens*, *Agropyron repens*, and *Agropyron tsukushiense* var. transiens Ohwi.

In addition, they also show excellent herbicidal and regrowth-control effects on, for example, perennial weeds, such as Johnson grass and *Cynodon dactylon* Parsoon.

The active compounds according to the present invention may be used as selective herbicides in many cultures. As examples the following cultures may be mentioned: beans, cotton, carrot, potato, beet, cabbage, mustard, peanut, radish, tobacco, tomato and cucumber.

The active compounds according to the present invention can be converted into customary formulations using agriculturally acceptable adjuvants by methods generally practiced in the production of agricultural chemicals, In actual use, the herbicidal compositions in various forms are applied either directly or after diluting them with water to the desired concentrations. Examples of the agriculturally acceptable adjuvants, as referred to herein, are diluents (solvents, extenders, carriers), surface-active agents (solubilizing agents, emulsifiers, dispersants, wetting agents), stabilizers, stickers, aerosol propellants, and synergists.

Examples of the solvents are water, and organic solvents, for example hydrocarbons [e.g., n-hexane, petroleum ether, naphtha, petroleum fractions (e.g., paraffin waxes, kerosene, light oils, middle oils, heavy oils), benzene, toluene, and xylenes], halogenated hydrocarbons [e.g., methylene chloride, carbon tetrachloride, trichloroethylene, ethylene chloride, ethylene dichloride, chlorobenzene and chloroform], alcohols [e.g. methyl alcohol, ethyl alcohol, propyl alcohol and ethylene glycol], ethers [e.g., ethyl ether, ethylene oxide and dioxane], alcohol ethers [e.g., ethylene glycol monomethyl ether], ketones [e.g., acetone and isophorone], esters [e.g., ethyl acetate and amyl acetate], amides [e.g., dimethylformamide and dimethylacetamide] and sulfoxides [e.g., dimethyl sulfoxide].

Examples of the extenders or carriers include inorganic powders, for example slaked lime, magnesium lime, gypsum, calcium carbonate, silica, perlite, pumice, calcite, diatomaceous earth, amorphous silica, alumina, zeolites, and clay minerals (e.g., pyrophyllite, talc, montmorrillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfuric acid esters (e.g., sodium laurylsulfate), arylsulfonic acid salts (e.g., alkylarylsulfonic acid salts and sodium alkylnaphthalenesulfonates), succinic acid salts and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (e.g., agricultural soaps, casein lime, sodium alginate, polyvinyl alcohol, vinyl acetate-type adhesives and acrylic adhesives); effect-prolonging agents; dispersion stabilizers (e.g., casein, Tragacanth, carboxymethyl cellulose and polyvinyl alcohol); and synergists.

The active compounds according to this invention can be converted into the customary formulations, such as emulsifiable concentrates, oils, wettable powders, soluble powders, suspensions, dusts, granules and pulverulent compositions. These formulations may be produced in known manner.

The amount of active compound in the ready-to-use preparation can vary widely according to circumstance. However, it is in general from 0.001 to about 100 percent by weight of active compound, preferably from about 0.005 to 95 percent by weight.

In actual use, the suitable amount of the active compound in the aforesaid compositions of various forms and ready-to-use preparations is, for example, about 0.01 to about 95% by weight, preferably about 0.05 to about 60% by weight.

The content of the active ingredient can be properly varied depending upon the form of the preparation or composition, the method, purpose, time and focus of its application, the state of occurrence of weeds, etc.

If required, the compound of this invention may be used further in combination with other agricultural chemicals, for example insecticides, fungicides, miticides, nematocides, antiviral agents, other herbicides, plant growth regulators and attractants [e.g., organophosphorus ester compounds, organic chlorine compounds, dinitro compounds, organic sulfur or metal compounds, antibiotics, substituted diphenyl ether compounds, urea compounds, and triazine compounds], and/or fertilizers.

Various compositions and ready-to-use preparations containing the aforesaid active ingredient can be applied by various methods generally practiced in the field of agricultural chemical application, for example dispersing (liquid spraying, misting, atomizing, dust dispersing, granule dispersing, water surface application and pouring); and soil application (mixing with the soil, and sprinkling). They can also be used by the so-called ultralow volume spraying method. According to this method, the active ingredient may be included in an amount of 100%.

The rate of application per unit area is, for example, about 0.01 to about 2.0 kg, preferably about 0.05 to about 1.0 kg, per hectare. In special cases, however, it may, and sometimes should, be outside the specified range.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

It will be seen that the usual methods of providing a harvested crop may be improved by the present invention.

Compositions according to this invention are illustrated in the following Examples. It should be noted, however, that the invention is not limited to these specific examples alone.

In these Examples, the compounds according to the present invention are each identified by the number (given in brackets) of the corresponding preparative Example. References to "parts" are to be understood as meaning parts by weight.

EXAMPLE I

Wettable powder

Fifteen parts of compound (1), 80 parts of a 1:5 mixture of powdered diatomaceous earth and powdered clay, 2 parts of sodium alkylbenzenesulfonate and 3 parts of sodium alkylnaphthalenesulfonate/formaldehyde condensate were ground and mixed to form a wettable powder. The wettable powder was diluted with water before use.

EXAMPLE II

Emulsifiable concentrate

Thirty parts of compound (2), 55 parts of xylene, 8 parts of polyoxyethylene alkylphenyl ether and 7 parts of calcium alkylbenzenesulfonate were mixed with stirring to form an emulsifiable concentrate. The emulsifiable concentrate was diluted with water before use.

EXAMPLE III

Dust

Two parts of compound (3) and 98 parts of powdered clay were pulverized and mixed to form a dusting agent.

EXAMPLE IV

Dust 1.5 parts of compound (4), 0.5 parts of isopropyl hydrogen phosphate (PAP) and 98 parts of powdered clay were ground and mixed to form a dusting agent.

EXAMPLE V

Granules 25 parts of water were added to, and thoroughly mixed with, a mixture of 10 parts of compound (5), 30 parts of bentonite (montmorillonite), 58 parts of talc and 2 parts of lignin sulfonate. The resultant mixture was formed into granules having a size of 10 to 40 mesh by means of an extrusion-type granulator, and dried at 40° to 50° C. to form granules.

EXAMPLE VI

Granules

A rotary mixer was charged with 95 parts of clay mineral particles having a particle size distribution in the range of 0.2 to 2 mm, and, while rotating the mixer, 5 parts of compound (6) dissolved in an organic solvent were sprayed uniformly onto the clay mineral particles. The particles were then dried at 40° to 50° C. to form granules.

The herbicidal activity of the compounds of the formula (I) is illustrated by the following biotest Examples.

In these Examples, the compounds according to the present invention are each identified by the number (given in brackets) of the corresponding preparative Example.

The known comparison compounds are identified as follows:

EXAMPLE A

Pre-emergence treatment tests for weeds and crops in upland fields:

Preparation of active compound:
Carrier: 5 parts by weight of acetone
Emulsifier: 1 part by weight of benzyloxy polyglycol ether A preparation of the active compound was obtained as an emulsifiable concentrate by mixing 1 part by weight of the active compound with the aforesaid amounts of the carrier and the emulsifier. A predetermined amount of the preparation was obtained by dilution with water. Testing method:

Field soils placed in 1,000 cm$^2$ pots were respectively seeded with Arachis (peanut), Pisum (garden pea), Gossypium (cotton) and Glycine (Soya bean) in a greenhouse, and covered with a soil mixed with seeds of *Agropyron repens, Echinochloa crus-galli* and *Setaria lutescens* in a depth of 1 cm. One day after the seeding, 10 ml of the above-prepared solutions respectively containing 200 ppm of the active ingredient were sprayed uniformly to the soil surface layer.

4 weeks after the treatment, the herbicidal effect and degree of phytotoxicity were evaluated on a scale of from 0 to 10 in accordance with the following standards.

The herbicidal effect was evaluated as follows in comparison with an untreated control.

| Rating | Weed-kill ratio based on the control |
|--------|---------------------------------------|
| 10 | 100% (withered) |
| 9 | at least 90% but less than 100% |
| 8 | at least 80% but less than 90% |
| 7 | at least 70% but less than 80% |
| 6 | at least 60% but less than 70% |
| 5 | at least 50% but less than 60% |
| 4 | at least 40% but less than 50% |
| 3 | at least 30% but less than 40% |
| 2 | at least 20% but less than 30% |
| 1 | at least 10% but less than 20% |
| 0 | less than 10% (not effective) |

(A-1) = CF$_3$—C$_6$H$_4$—O—C$_6$H$_4$—O—CH(CH$_3$)—C(O)—O—(CH$_2$)$_2$—S—CH$_3$ (known from DE-OS 2,617,804)

(A-2) = CF$_3$—C$_6$H$_4$—O—C$_6$H$_4$—O—CH(CH$_3$)—C(O)—O—(CH$_2$)$_2$—SO$_2$—CH$_3$ (known from DE-OS 2,617,804)

(A-3) = CF$_3$—C$_6$H$_4$—O—C$_6$H$_4$—O—CH(CH$_3$)—C(O)—O—(CH$_2$)$_2$—S—CH(CH$_3$)$_2$ (known from DE-OS 2,617,804)

(B-1) = CF$_3$—C$_5$H$_3$N—O—C$_6$H$_4$—O—CH(CH$_3$)—C(O)—O—(CH$_2$)$_2$—O—C$_2$H$_5$ (known from DE-OS 2,812,571).

The phytotoxicity towards the crops was evaluated as follows in comparison with the untreated control.

| Rating | Phytotoxicity rate in comparison with the control |
|---|---|
| 10 | at least 90% (fatal damage) |
| 9 | at least 80% but less than 90% |
| 8 | at least 70% but less than 80% |
| 7 | at least 60% but less than 70% |
| 6 | at least 50% but less than 60% |
| 5 | at least 40% but less than 50% |
| 4 | at least 30% but less than 40% |
| 3 | at least 20% but less than 30% |
| 2 | at least 10% but less than 20% |
| 1 | more than 0% but less than 10% |
| 0 | 0% (no phytotoxicity) |

The test results are given in Table 1.

TABLE 1

| Compound No. | Amount of the active ingredient (kg/ha) | Herbicidal Effect Weeds | | | Phytotoxicity Crops | | | |
|---|---|---|---|---|---|---|---|---|
| | | Agropyron repens | Echinochloa crus-galli | Setaria lutescens | Peanut | Garden pea | Cotton | Soybean |
| 1 | 0.2 | 10 | 10 | 10 | 0 | 0 | 0 | 0 |
| 3 | 0.2 | 10 | 10 | 10 | 0 | 0 | 0 | 0 |
| 4 | 0.2 | 10 | 10 | 10 | 0 | 0 | 0 | 0 |
| 12 | 0.2 | 10 | 10 | 10 | 0 | 0 | 0 | 0 |
| 20 | 0.2 | 10 | 10 | 10 | 0 | 0 | 0 | 0 |
| 22 | 0.2 | 10 | 10 | 10 | 0 | 0 | 0 | 0 |
| (A-1) (known) | 0.2 | 3 | 4 | 4 | 0 | 0 | 0 | 0 |

EXAMPLE B

Foliage-treating tests for weeds and crops in upland fields:

Field soils placed in 2,000 cm² pots were respectively seeded with Glycine (Soya bean), Rephanus (radish) and Beta (beet), and covered with a soil mixed with seeds of *Echinochloa crus-galli*, *Digitaria adscendens*, *Eleusine indica*, *Setaria viridis*, *Avena fatua* and *Alopecurus aequalis* (var. *amurensis Ohwi*) in a depth of 1 cm. 10 days after seeding (when weeds were on the average in a second leaf stage and when Glycine, Rephanus and Beta were in the initial stage of normal leaf-growing period), 20 ml of the solutions prepared as in Test Example A and respectively containing 100 ppm of the active ingredient were uniformly sprayed to the leaves of the plants to be tested.

3 weeks after the treatment, the herbicidal effect and degree of phytotoxicity were evaluated in the same manner as in Example A.

The test results are shown in Table 2.

TABLE 2

| Compound No. | Amount of the active ingredient (kg/ha) | Herbicidal Effect Weeds | | | | | | Phytotoxicity Crops | | |
|---|---|---|---|---|---|---|---|---|---|---|
| | | Echinochloa crus-galli | Digitaria adscendens | Eleusine indica | Setaria viridis | Avena fatua | Alopecurus aequalis | Soybean | Radish | Beet |
| 2 | 0.1 | 10 | 10 | 10 | 10 | 10 | 10 | 0 | 0 | 0 |
| 5 | 0.1 | 10 | 10 | 10 | 10 | 10 | 10 | 0 | 0 | 0 |
| 6 | 0.1 | 10 | 10 | 10 | 10 | 10 | 10 | 0 | 0 | 0 |
| 7 | 0.1 | 10 | 10 | 10 | 10 | 10 | 10 | 0 | 0 | 0 |
| 8 | 0.1 | 10 | 10 | 10 | 10 | 10 | 10 | 0 | 0 | 0 |
| 9 | 0.1 | 10 | 10 | 10 | 10 | 10 | 10 | 0 | 0 | 0 |
| 11 | 0.1 | 10 | 10 | 10 | 10 | 10 | 10 | 0 | 0 | 0 |
| 12 | 0.1 | 10 | 10 | 10 | 10 | 10 | 10 | 0 | 0 | 0 |
| 13 | 0.1 | 10 | 10 | 10 | 10 | 10 | 10 | 0 | 0 | 0 |
| 14 | 0.1 | 10 | 10 | 10 | 10 | 10 | 10 | 0 | 0 | 0 |
| 16 | 0.1 | 10 | 10 | 10 | 10 | 10 | 10 | 0 | 0 | 0 |
| 18 | 0.1 | 10 | 10 | 10 | 10 | 10 | 10 | 0 | 0 | 0 |
| 19 | 0.1 | 10 | 10 | 10 | 10 | 10 | 10 | 0 | 0 | 0 |
| 20 | 0.1 | 10 | 10 | 10 | 10 | 10 | 10 | 0 | 0 | 0 |
| 21 | 0.1 | 10 | 10 | 10 | 10 | 10 | 10 | 0 | 0 | 0 |
| 22 | 0.1 | 10 | 10 | 10 | 10 | 10 | 10 | 0 | 0 | 0 |
| 23 | 0.1 | 10 | 10 | 10 | 10 | 10 | 10 | 0 | 0 | 0 |
| 24 | 0.1 | 10 | 10 | 10 | 10 | 10 | 10 | 0 | 0 | 0 |
| (A-1) | 0.1 | 3 | 2 | 2 | 3 | 1 | 3 | 0 | 0 | 0 |
| (A-2) | 0.1 | 3 | 1 | 1 | 2 | 1 | 2 | 0 | 0 | 0 |

EXAMPLE C

Herbicidal and regrowth-control tests for *Agropyron tsukushiense var. transiens Ohwi*:

Rice field where *Agropyron tsukushiense* was gregarious was divided into 1 m² sections. 100 ml portions of solutions prepared as in Example A and respectively containing 200 ppm of the active ingredient were sprayed to the foliage of *Agropyron tsukushiense* in each section. 20 days after the treatment, the herbicidal effects were evaluated in the same manner as in Example A. Further, the effect of controllowing regrowth of *Agropyron tsukushiense* was evaluated 40 days and 60 days after the treatment in accordance with the following standards.

| Rating | Regrowth-control ratio based on untreated section |
|---|---|
| 10 | 100% (complete control of regrowth) |
| 9 | at least 90% but less than 100% |
| 8 | at least 80% but less than 90% |
| 7 | at least 70% but less than 80% |

-continued

| Rating | Regrowth-control ratio based on untreated section |
|---|---|
| 6 | at least 60% but less than 70% |
| 5 | at least 50% but less than 60% |
| 4 | at least 40% but less than 50% |
| 3 | at least 30% but less than 40% |
| 2 | at least 20% but less than 30% |
| 1 | at least 10% but less than 20% |
| 0 | less than 10% (no regrowth-control effect) |

The test results are shown in Table 3.

TABLE 3

| Compound No. | Amount of the active ingredient (kg/ha) | Herbicidal Effect (20 days after spraying) | Regrowth-control Effect | |
|---|---|---|---|---|
| | | | 40 days after spraying | 60 days after spraying |
| 1 | 0.2 | 10 | 10 | 10 |
| 2 | 0.2 | 10 | 10 | 10 |
| 12 | 0.2 | 10 | 10 | 10 |
| 23 | 0.2 | 10 | 10 | 10 |
| A-3 (known) | 0.2 | 4 | 2 | 0 |
| B-1 (known) | 0.2 | 6 | 2 | 0 |

EXAMPLE D

Herbicidal and regrowth-control test for Cynodon dactylon:

Upland field where Cynodon dactylon was gregarious was divided into 1 m² sections. The active ingredient in the same quantity as in Example C was treated to the Cynodon dactylon.

Herbicidal effect was evaluated 20 days after the treatment, and regrowth-control effect was evaluated 40 days and 60 days after the treatment in accordance with the same manner as in the foregoing Examples A to C.

The test results are shown in Table 4.

TABLE 4

| Compound No. | Amount of the active ingredient (kg/ha) | Herbicidal Effect (20 days after spraying) | Regrowth-control Effect | |
|---|---|---|---|---|
| | | | 40 days after spraying | 60 days after spraying |
| 3 | 0.2 | 10 | 10 | 10 |
| 21 | 0.2 | 10 | 10 | 10 |
| 22 | 0.2 | 10 | 10 | 10 |
| A-3 (known) | 0.2 | 3 | 1 | 0 |
| B-1 (known) | 0.2 | 6 | 3 | 0 |

The following examples serve to illustrate processes for the production of compounds according to the present invention.

PREPARATIVE EXAMPLES

EXAMPLE 1

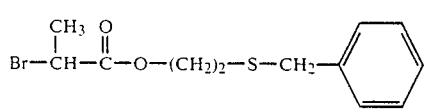

(III-1)

A solution of 21.6 g of 2-bromopropionyl bromide in 30 ml of toluene was added dropwise to a solution of 10.1 g of triethylamine and 16.8 g of 2-benzylthioethanol in 150 ml of toluene at room temperature whilst stirring. After the addition was completed, the reaction mixture was stirred for a further 2 hours at room temperature. The mixture was then washed successively with 1% strength by weight aqueous solution of sodium hydroxide and water. After drying the organic phase over anhydrous sodium sulphate, the toluene was distilled off under reduced pressure, and the end product of 2-benzylthioethyl 2-bromopropionate was obtained in a yield of 28.8 g as a colorless product. $n_D^{20} = 1.5570$.

EXAMPLE 2

In the same manner as described in Example 1, there were obtained the compounds of the present invention, which are shown in the following Table 5.

TABLE 5

$$Z^1-\underset{\underset{CH_3}{|}}{CH}-\underset{\underset{O}{||}}{C}-O-\underset{\underset{R}{|}}{CH}(CH_2)_m-S(O)_n-CH_2-\underset{\phantom{X}}{\bigcirc}X_a \quad (III)$$

| Compound No. | $Z^1$ | R | m | n | $X_a$ | Physical Constant |
|---|---|---|---|---|---|---|
| III-2 | Br | H | 1 | 0 | 2-F | $n_D^{20}$ 1.5422 |
| III-3 | Br | H | 1 | 0 | 4-Cl | $n_D^{20}$ 1.5650 |
| III-4 | Br | H | 1 | 0 | 2,4-Cl$_2$ | $n_D^{20}$ 1.5729 |
| III-5 | Br | H | 1 | 0 | 4-OCH$_3$ | $n_D^{20}$ 1.5600 |
| III-6 | Br | H | 1 | 0 | 3-NO$_2$ | $n_D^{20}$ 1.5749 |
| III-7 | Br | H | 1 | 0 | 4-CH$_3$ | $n_D^{20}$ 1.5538 |
| III-8 | Br | H | 1 | 1 | H | oil |
| III-9 | Br | —CH$_3$ | 1 | 0 | H | $n_D^{20}$ 1.5465 |
| III-10 | Br | H | 2 | 0 | H | $n_D^{20}$ 1.5510 |
| III-11 | Cl | H | 1 | 0 | H | $n_D^{20}$ 1.5451 |
| III-12 | Cl | H | 1 | 2 | H | oil |
| III-13 | Cl | —CH$_3$ | 1 | 0 | H | $n_D^{20}$ 1.5387 |
| III-14 | Cl | H | 1 | 0 | 2-F | $n_D^{20}$ 1.5330 |
| III-15 | Cl | H | 1 | 0 | 2-Cl | oil |

EXAMPLE 3

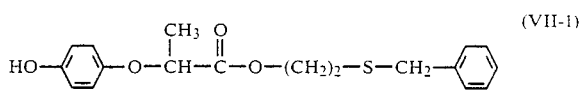

(VII-1)

12,1 g of hydroquinone were dissolved in 60 ml of dry dimethylformamide, and while blowing a slow stream of nitrogen into the solution, 31,7 g of potassium carbonate were added thereto at room temperature whilst stirring. Then the mixture was heated to 90° to 95° C. for one hour with stirring. The mixture was cooled to 60° C., and 30.3 g of 2-benzylthioethyl 2-bromopropionate were added dropwise thereto. After the addition was completed, the mixture was further heated to 90° C. for 2 hours. After cooling the reaction mixture to room temperature, it was poured into ice-water and adjusted to pH 7. Then it was extracted with 100 ml of chloroform. The organic phase was dried and the chloroform was distilled off under reduced pressure. The end product of 2-benzylthioethyl 2-(4-hydroxy-phenoxy)-propionate was obtained in a yield of 25.2 g in the form of a brown oil. $n_D^{20} = 1.5706$.

EXAMPLE 4

In the same manner as described in Example 3, there were obtained the compounds of the present invention, which are shown in the following Table 6.

TABLE 6

| Compound No. | Starting material | Starting material | Product of general formula (VII) |
|---|---|---|---|
| VII-2 | Hydroquinone | 2-(2-fluorobenzylthio)ethyl 2-bromopropionate | 2-(2-fluorobenzylthio)ethyl 2-(4-hydroxylphenoxy)-propionate $n_D^{20} = 1.5585$ |
| VII-3 | Hydroquinone | 2-(4-chlorobenzylthio)ethyl 2-bromopropionate | 2-(4-chlorobenzylthio)ethyl 2-(4-hydroxyphenoxy)-propionate $n_D^{20} = 1.5789$ |
| VII-4 | Hydroquinone | 2-(2,4-dichlorobenzylthio)-ethyl 2-bromopropionate | 2-(2,4-dichlorobenzylthio)-ethyl 2-(4-hydroxyphenoxy)-propionate |
| VII-5 | Hydroquinone | 2-(4-methoxybenzylthio)-ethyl 2-bromopropionate | 2-(4-methoxybenzylthio)-ethyl 2-(4-hydroxyphenoxy)-propionate |
| VII-6 | Hydroquinone | 2-(3-nitrobenzylthio)ethyl 2-bromopropionate | 2-(3-nitrobenzylthio)ethyl 2-(4-hydroxyphenoxy)-propionate |
| VII-7 | Hydroquinone | 2-(4-methylbenzylthio)ethyl 2-bromopropionate | 2-(4-methylbenzylthio)ethyl 2-(4-hydroxyphenoxy)-propionate |
| VII-8 | Hydroquinone | 2-benzylsulfinylethyl 2-bromopropionate | 2-benzylsulfinylethyl 2-(4-hydroxyphenoxy)propionate |
| VII-9 | Hydroquinone | 1-methyl-2-benzylthio-ethyl 2-bromopropionate | 1-methyl-2-benzylthioethyl 2-(4-hydroxyphenoxy)-propionate $n_D^{20} = 1.5687$ |
| VII-10 | Hydroquinone | 3-benzylthiopropyl 2-bromopropionate | 3-benzylthiopropyl 2-(4-hydrozyphenoxy)propionate $n_D^{19} = 1.5672$ |
| VII-11 | Hydroquinone | 2-(2-chlorobenzylthio)ethyl 2-chloropropionate | 2-(2-chlorobenzylthio)ethyl 2-(4-hydroxyphenoxy)-propionate |
| VII-12 | Hydroquinone | 2-benzylsulfonylethyl 2-chloropropionate | 2-benzylsulfonylethyl 2-(4-hydroxyphenoxy)-propionate |

EXAMPLE 5

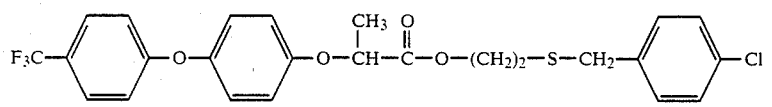

(Compound No. 1)

A mixture consisting of 25.4 g of 4-(4-trifluoromethylphenoxy)phenol, 14.5 g of anhydrous potassium carbonate, 33.8 g of 2-(4-chlorobenzylthio)ethyl 2-bromopropionate and 150 ml of dry acetonitrile was refluxed for 3 hours with vigorous stirring. After cooling the reaction mixture to room temperature, the acetonitrile was removed under reduced pressure. Then, 150 ml of toluene were added to the residue and the resulting mixture was washed successively with 1% strength by weight aqueous sodium hydroxide solution and water, followed by dehydration. Upon distilling off the toluene under reduced pressure, there were obtained 46.4 g of 2-(4-chlorobenzylthio)-ethyl 2-[4-(4-trifluoromethylphenoxy)-phenoxy]-propionate in the form of a colorless oil. $n_D^{20} = 1.5555$.

EXAMPLE 6

In the same manner as described in Example 5, there were obtained the compounds of the present invention, which are shown in the following Table 7.

TABLE 7

$$\text{Ar}-\text{O}-\underset{}{\bigcirc}-\text{O}-\underset{\text{CH}_3}{\overset{}{\text{CH}}}-\underset{\text{O}}{\overset{\|}{\text{C}}}-\text{O}-\underset{R}{\overset{}{\text{CH}}}(\text{CH}_2)_m-\text{S}((\text{O}))_n-\text{CH}_2-\underset{}{\bigcirc}-X_a \quad (I)$$

| Compound No. | Ar | R | m | n | $X_a$ | Physical Constant |
|---|---|---|---|---|---|---|
| 2 | F$_3$C—⟨◯⟩— | H | 1 | 0 | H | $n_D^{20}$ 1.5495 |
| 3 | F$_3$C—⟨◯⟩— | —CH$_3$ | 1 | 0 | H | $n_D^{20}$ 1.5436 |

TABLE 7-continued $$\text{Ar—O—}\underset{}{\bigcirc}\text{—O—}\underset{CH_3}{\underset{|}{CH}}-\underset{O}{\overset{\|}{C}}-O-\underset{R}{\underset{|}{CH}}(CH_2)_m-S((O))_n-CH_2-\underset{}{\bigcirc}X_a \quad (I)$$

| Compound No. | Ar | R | m | n | $X_a$ | Physical Constant |
|---|---|---|---|---|---|---|
| 4 | F$_3$C—⌬— | H | 2 | 0 | H | $n_D^{20}$ 1.5470 |
| 5 | F$_3$C—⌬— | H | 1 | 0 | 2-F | $n_D^{20}$ 1.5425 |
| 6 | F$_3$C—⌬— | H | 1 | 0 | 2-Cl | $n_D^{20}$ 1.5523 |
| 7 | F$_3$C—⌬— | H | 1 | 0 | 4-OCH$_3$ | $n_D^{20}$ 1.5520 |
| 8 | (3,5-dichloropyridyl) | H | 1 | 0 | 4-OCH$_3$ | $n_D^{20}$ 1.5927 |
| 9 | F$_3$C—⌬— | H | 1 | 0 | 2,4-Cl$_2$ | $n_D^{20}$ 1.5600 |
| 10 | (2-CF$_3$-4-Cl-phenyl) | H | 1 | 0 | H | $n_D^{20}$ 1.5583 |
| 11 | F$_3$C—⌬— | H | 1 | 0 | H | m.p. 126–127° C. |

EXAMPLE 7

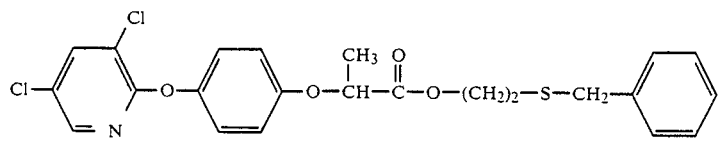

A solution of 34.7 g of 2-[4-(3,5-dichloro-2-pyridyloxy)-phenoxy]-propionyl chloride in 80 ml of toluene was added dropwise at 0° to 10° C. to a solution of 16.8 g of 2-benzylthioethanol and 10.1 g of triethylamine in 100 ml of toluene whilst stirring. After the addition was completed, the mixture was stirred further at 30° to 40° C. for 1 hour. The mixture was washed successively with a 1% aqueous solution of sodium hydroxide and water, and dried. Upon distilling off the toluene under reduced pressure, there were obtained 44.9 g of 2-benzylthioethyl 2-[4-(3,5-dichloro-2-pyridyloxy)-phenoxy]-propionate in the form of a colorless viscous oil. $n_D^{20}=1.5940$.

EXAMPLE 8

In the same manner as described in Example 7, there were obtained the following compounds of the present invention, which are shown in the following Table 8.

TABLE 8

$$\text{Ar}-\text{O}-\underset{}{\bigcirc}-\text{O}-\underset{\text{CH}_3}{\underset{|}{\text{CH}}}-\underset{\text{O}}{\overset{\|}{\text{C}}}-\text{O}-\underset{R}{\underset{|}{\text{CH}}}(\text{CH}_2)_m-\text{S}(\text{O})_n-\text{CH}_2-\underset{}{\bigcirc}-\text{X}_a \quad (\text{I})$$

| Compound No. | Ar | R | m | n | $X_a$ | Physical Constant |
|---|---|---|---|---|---|---|
| 13 | 3,5-dichloropyridin-2-yl | —CH₃ | 1 | 0 | H | $n_D^{20}$ 1.5825 |
| 14 | 3,5-dichloropyridin-2-yl | H | 2 | 0 | H | $n_D^{20}$ 1.5898 |
| 15 | 3,5-dichloropyridin-2-yl | H | 1 | 0 | 2-F | $n_D^{20}$ 1.5850 |
| 16 | 3,5-dichloropyridin-2-yl | H | 1 | 0 | 4-Cl | $n_D^{20}$ 1.5972 |
| 17 | 3,5-dichloropyridin-2-yl | H | 1 | 0 | 4-CH₃ | $n_D^{20}$ 1.5920 |
| 18 | 4-(trifluoromethyl)phenyl | H | 1 | 0 | 3-NO₂ | $n_D^{20}$ 1.5630 |
| 19 | 3,5-dichloropyridin-2-yl | H | 1 | 0 | 3-NO₂ | $n_D^{20}$ 1.6037 |
| 20 | 5-(trifluoromethyl)pyridin-2-yl | H | 1 | 0 | 4-OCH₃ | $n_D^{20}$ 1.5530 |

EXAMPLE 9

(Compound No. 21)

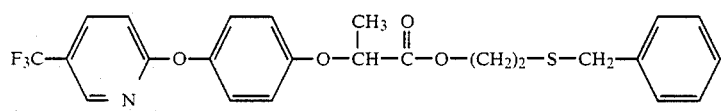

15.2 g of potassium carbonate were added to a solution of 33.2 g of 2-benzylthioethyl 2-(4-hydroxyphenoxy)-propionate in 100 ml of dimethyl sulfoxide at room temperature whilst stirring. The mixture was heated to 90° C. for 1 hour with stirring. Then, 20.0 g of 2-chloro-5-trifluoromethyl-pyridine were added thereto while maintaining the temperature between 80° and 90° C. After the addition was completed, the reaction mixture was further stirred at this temperature for 2 hours, and then cooled to room temperature. Then the reaction mixture was poured into ice water and extracted with chloroform. After drying the organic phase, the chloroform was removed under reduced pressure. There were obtained 36.3 g of 2-benzylthioethyl 2-[4-(5-trifluoromethyl-2-pyridyloxy)-phenoxy]-propionate in the form of a pale yellow viscous oil. $n_D^{20}=1.5505$.

EXAMPLE 10

In the same manner as described in Example 9, there were obtained the following compounds of the present invention, which are shown in the following Table 9.

TABLE 9

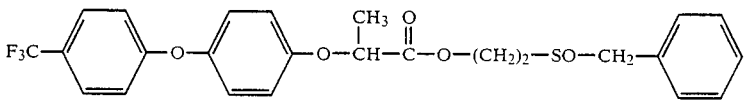

| Compound No. | Ar | R | m | n | $X_a$ | Physical Constant |
|---|---|---|---|---|---|---|
| 22 | F₃C—⟨pyridyl⟩ | H | 1 | 0 | 2-F | $n_D^{20}$ 1.5430 |
| 23 | F₃C—⟨pyridyl⟩ | H | 1 | 0 | 4-Cl | $n_D^{20}$ 1.5566 |
| 24 | Cl,Cl—⟨pyridyl⟩ | H | 1 | 0 | 2,4-Cl₂ | $n_D^{20}$ 1.6025 |

EXAMPLE 11

(Compound No. 25)

F₃C—⟨C₆H₄⟩—O—⟨C₆H₄⟩—O—CH(CH₃)—C(O)—O—(CH₂)₂—SO—CH₂—⟨C₆H₅⟩

10.7 g of 35% aqueous hydrogen peroxide were added dropwise to a solution of 47.6 g of 2-benzylthioethyl 2-[4-(4-trifluoromethylphenoxy)-phenoxy]-propionate in 200 ml of acetic acid at 20° to 30° C. whilst stirring. Since the reaction was exothermic, it was carried out with cooling. After the addition was completed, the mixture was stirred for a further 4 hours at the same temperature. Then, the reaction mixture was poured into ice water, and extracted with chloroform. After drying the organic phase, the chloroform was removed under reduced pressure. There were obtained 46.7 g of 2-benzylsulfinylethyl 2-[3-(4-trifluoromethylphenoxy)-phenoxy]-propionate in the form of a viscous oil. On standing, this compound gradually solidified and showed a melting point of 110° to 112° C.

It will be understood that the specification and examples are illustrative but not limitative of the present invention and that other embodiments within the spirit and scope of the invention will suggest themselves to those skilled in the art.

What is claimed is:

1. Substituted phenoxypropionates of the formula

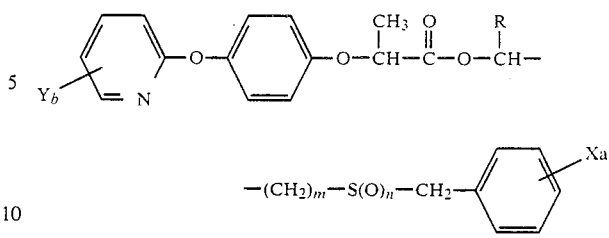

in which
Y represents a halogen atom or a trifluoromethyl group and
b is 1 or 2,
R represents a hydrogen atom or a methyl group,
X represents a hydrogen atom, a halogen atom, a nitro group, a lower alkyl group or a lower alkoxy group,
a and m independently is 1 or 2, and
n is 1 or 2.

2. Compound as claimed in claim 1, wherein R is a hydrogen atom.

3. Compound as claimed in claim 1, wherein R is a methyl group.

4. Compound as claimed in claim 1, wherein X is a hydrogen atom.

5. Compound as claimed in claim 1, wherein X is a halogen atom.

6. Compound as claimed in claim 1, wherein X is a nitro group.

7. Compound as claimed in claim 1, wherein X is a lower alkyl group.

8. Compound as claimed in claim 1, wherein X is a lower alkoxy group.

9. Compound as claimed in claim 1,
in which
Y is fluorine, chlorine, bromine, iodine or a trifluoromethyl group, and
X is hydrogen atom, fluorine, chlorine, bromine, iodine, a nitro group, a methyl, ethyl, propyl, isopropyl, n-butyl, iso-butyl, sec.-butyl or tert.-butyl group, or a methoxy, ethoxy, n-propoxy, isopropoxy, n-butoxy, iso-butoxy, sec-butoxy or tert.-butoxy group.

10. A herbicidal composition comprising an agriculturally acceptable carrier and, in herbicidally effective amount, a substituted phenoxypropionate as claimed in claim 1.

11. A herbicidal composition as claimed in claim 10, containing from 0.01 to 95% of the active compound, by weight.

12. A method of combating weeds which comprises applying to the weeds, or their habitat, a herbicidally effective amount of a substituted phenoxypropionate as claimed in claim 1.

13. A method as claimed in claim 12, wherein said compound is applied at a dosage of 0.01 to 2.0 kg per hectare.

14. A method as claimed in claim 13, wherein said compound is applied at a dosage of 0.05 to 1.0 kg per hectare.

* * * * *